United States Patent [19]

Mikkelsen

[11] Plant 4,000

[45] Dec. 28, 1976

[54] POINSETTIA PLANT

[75] Inventor: James C. Mikkelsen, Ashtabula, Ohio

[73] Assignee: Mikkelsens, Inc., Ashtabula, Ohio

[21] Appl. No.: 663,130

[22] Filed: Mar. 2, 1976

[51] Int. Cl.[2] ..... A01H 5/00

[52] U.S. Cl. ..... Plt./86

[58] Field of Search ..... Plt./86

*Primary Examiner*—Robert E. Bagwill

*Attorney, Agent, or Firm*—Donald D. Jeffery

CLAIM

A new and distinct cultivar of poinsettia plant characterized by the combined characteristics of growth as a single stem or pinched plant; superior growth habit and vigor; large light pink bracts which are broad, thick and self supporting, with the bract head of single stem plants measuring up to 40 cm. in diameter; large cyathias which indicate an increase in ploidy from diploid to tetraploid; long lasting bracts and foliage, and by its relatively slower rooting habits.

1 Drawing Figure

The present invention relates to a new and distinctive cultivar of poinsettia plant known by the varietal name Imperial, and botanically known as *Euphorbia pulcherrima.*

The new cultivar is a mutation of a non-commercialized, non-patented tetraploid mutation of Mikkel Rochford found in England in 1968. Mikkel Rochford in turn is a non-patented cultivar of the cultivar Paul Mikkelsen, disclosed in U.S. Plant Pat. No. 2,328. A series of red tetraploids were isolated from the original Rochford clone at Mikkelsens, Inc., Ashtabula, Ohio in the years 1971–1973 and from one of these selections a side branch with light colored stems appeared that when flowered in the winter of 1973–1974 gave pink colored bracts.

The new cultivar has been asexually reproduced by cuttings in the greenhouses of Mikkelsens, Inc., Ashtabula, Ohio during 1975. Several hundred cuttings all came true to type, and the new cultivar has therefore been found to retain its distinctive characteristics through successive propagations.

The following characteristics in combination distinguish the new cultivar from its parent and from other poinsettias commercially known and used in the floriculture industry:

1. Although there is some similarity between the general appearance of Imperial to the cultivar Mikkelpink, U.S. Plant Pat. No. 2,501, the new cultivar has an overall stronger growth habit.

2. Imperial can be grown as a single stem or pinched plant, thereby giving it more versatility than Mikkelpink but being comparable to the unpatented cultivar Mikkel Pink Rochford.

3. The overall vigor of Imperial is greater than that of Mikkelpink and the present branching cultivars Pink Annette Hegg, Mikkel Pink Rochford, or Mikkel Fantastic, disclosed in U.S. Plant Pat. No. 3,721, issued May 20, 1975 to P. J. Murison.

4. The large light pink bracts are quite broad, thick and self supporting. Single stem plants display a large bract head measuring upwards of 40 cm. in diameter.

5. The cyathias are much larger than the above named cultivars, clearly indicating an increase in ploidy from diploid to tetraploid.

6. Both bracts and foliage are long lasting, a general characteristic of the Paul Mikkelsen cultivar and its many mutations.

7. Stock plants are not as prolific in cutting production as in the original Mikkel Rochford cultivar, but ample for economic production.

8. Rooting in the summer is generally 5–7 days slower than for the Mikkel Rochford or Hegg varieties and may be 10–14 days slower in the winter months.

9. Under controlled manipulation of daylength, flowering generally takes place in 10 weeks compared to nine weeks for Mikkel Pink Rochford.

10. The cyathias tend to remain longer in the bract head when plants are placed in the house than those of Mikkel Pink Rochford or Mikkelpink.

11. Imperial and Triumph, disclosed in my pending application Ser. No. 575,435, filed May 7, 1975, are very similar in most respects except color, and will complement each other in most commercial production programs.

The accompanying colored photographic drawing illustrates the foliage and bracts of the new cultivar, with the colors being as true as possible to obtain in color reproductions of this type.

The following is a detailed description of the new cultivar based on plants produced under commercial practices in the greenhouses of Mikkelsens, Inc., Ashtabula, Ohio. Color references are to the Royal Horticultural Society Colour Chart except where general color terms of ordinary dictionary significance are used.

Parentage: A mutation of a tetraploid clone of Mikkel Rochford.

Form of Plant: Upright, self supporting. Height of plant can be regulated by propagation timing and/or growth regulators. Plants grown without a pinch planted in 6″ pots in Ohio from Sept. 20–25, 1975 flowered Dec. 5, 1975 and were 35–40 cm. high and had stems 8–10 mm. in diameter.

Growth Habit: Slower, compact growth than Mikkel Rochford, with same self branching under high light conditions; breaks well after removal of terminal apex; vigorous heavy stems.

Rooting: When propagated directly in 2″ plastic pots using 50% perlite and 50% peat moss under controlled misting at 20°–22° C, rooting is in 25–27 days. Roots are thicker than Mikkel Pink Rochford and highly resistant to root rot organisms.

Blooming Habit: Natural flowering annually as daylength is reduced to 11 hours and night temperatures are uniformly at 18° C average.

Blooming Season: Natural blooming season occurs in early December in Ohio if 18° C night temperature is maintained. May be flowered in 70–75 days if environment is controlled for temperatures and day-length.

Foliage:

*Size.*—15–17 cm. long × 10–12 cm. wide with leaf petiole of last true leaves 8–10 cm. long.

*Quantity.*—Average to slightly above average when compared to the Paul Mikkelsen poinsettia and its mutations.

*Color.*—Upper side—dark green near 139-A. Under side—green near 146-B.

*Shape.*—Modified oakleaf with distinct sinuses in lower leaves evolving to ovate in terminal leaves at flowering.

*Texture.*—Upper side—smooth, veins slightly recessed. Under side—rough, veins protruding.

*Edge or margin.*—Some indentation approaching to entire.

*Aspect.*—Nearly horizontal to slight upward angle.

*Disease resistance.*—No occurrence of mildew or botrytis to date; outstanding leaf retention when plant is under adverse stress conditions.

Flower: (cyathia)

*Borne.*—In close clusters at the terminal of stem at flowering, further developing into tight racemes (usually three).

*Quantity.*—The number of cyathias is average for poinsettias and develop over a period of several months. Cyathias are large, up to 7 mm. in diameter, being green 138 A-B, and have usually two nectar cups, occasionally three, yellow 13-B.

*Bracts.*—Bracts are heavy, fleshy, self supporting, primary bracts are 15–17 cm. long and 12–13 cm. wide with petioles 2–3 cm. long; secondary toward elliptical 10–12 cm. long and 6–7 cm. wide with petiole 15 mm. to 20 mm. long. Total diameter of bract head is 35 upwards to 40 cm. in diameter.

*Color.*—Top—Very uniform red between 48C-D, fades slightly at maturity. Under—Distinctly soft red 38 B-C.

Reproductive Organs: Stamens predominate in early flowering, but pistels appear in secondary cyathias.

*Stamens.*—Color, yellow.

*Pollen.*—Color, yellow.

*Styles.*—Color, red.

*Ovaries.*—Color, green, develop three dark brown seeds.

In summary, the new cultivar can be described as a unique, high quality, attractive long lasting pink poinsettia with outstanding keeping qualities, and capable of being grown as large single stem specimen plants or compact strong vigorous pinched plants.

I claim:

1. A new and distinct cultivar of poinsettia plant characterized by the combined characteristics of growth as a single stem or pinched plant; superior growth habit and vigor; large light pink bracts which are broad, thick and self supporting, with the bract head of single stem plants measuring up to 40 cm. in diameter; large cyathias which indicate an increase in ploidy from diploid to tetraploid; long lasting bracts and foliage, and by its relatively slower rooting habits.

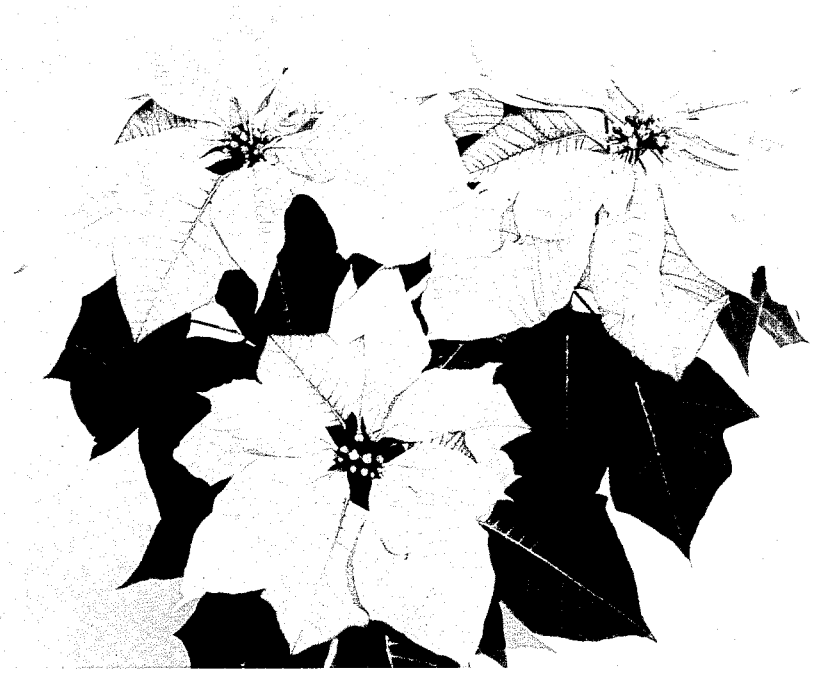

* * * * *